(12) United States Patent
Vacher et al.

(10) Patent No.: US 6,448,268 B1
(45) Date of Patent: Sep. 10, 2002

(54) ARYL-{4-FLUORO-4-[(2-PYRIDIN-2-YL-ETHYLAMINO)-METHYL]-PIPERIDIN-1-YL}-METHANONE DERIVATIVES AS 5-HT1 RECEPTOR ANTAGONISTS

(75) Inventors: Bernard Vacher, Castres; Bernard Bonnaud, Lagarrigues; Wouter Koek, Viviers-les-Montagnes, all of (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/807,102

(22) PCT Filed: Oct. 7, 1999

(86) PCT No.: PCT/FR99/02401

§ 371 (c)(1),
(2), (4) Date: May 29, 2001

(87) PCT Pub. No.: WO00/21953

PCT Pub. Date: Apr. 20, 2000

(30) Foreign Application Priority Data

Oct. 9, 1998 (FR) .............................................. 98 12660

(51) Int. Cl.[7] ..................... A61K 31/445; C07D 401/12
(52) U.S. Cl. .......................... 514/318; 546/194; 546/226
(58) Field of Search .......................... 514/318; 546/194, 546/226

(56) References Cited

U.S. PATENT DOCUMENTS 6,020,345 A * 2/2000 Vacher et al. ................ 514/318

OTHER PUBLICATIONS

Vacher et al. "Design and synthesis of a series of 6–substituted 2–pyridinylmethylamine derivatives as novel high affinity selective agonists at 5HT1A receptors" CA 130:66369 (1998).*

* cited by examiner

*Primary Examiner*—Ceila Chang
(74) *Attorney, Agent, or Firm*—The Firm of Hueschen and Sage; G. Patrick Sage

(57) ABSTRACT

The invention concerns novel aryl-{4-fluoro-4-[(2-pyridin-2-yl-ethylamino)-methyl]-piperidin-1-yl}-methanone derivatives of formula(1) wherein X is a hydrogen, fluorine or chlorine atom useful as medicines in particular having antidepressant, analgesic, anxiolytic and neuroprotective effects.

(1)

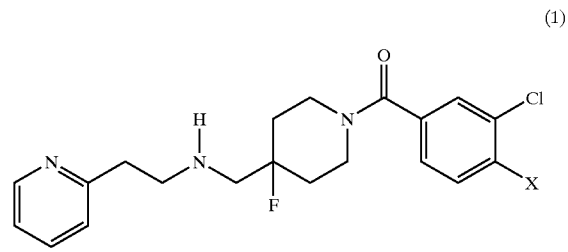

10 Claims, No Drawings

ARYL-{4-FLUORO-4-[(2-PYRIDIN-2-YL-ETHYLAMINO)-METHYL]-PIPERIDIN-1-YL}-METHANONE DERIVATIVES AS 5-HT1 RECEPTOR ANTAGONISTS

Serotonin (5-hydroxytryptamine, 5-HT) is a central nervous system neurotransmitter which exerts its many physiological functions by interaction with specific 5-HT receptors. These 5-HT receptors have been grouped into several main classes. Among these main classes, the 5-HT$_1$ class comprises receptors characterized by high affinity for serotonin. The 5-HT, class is itself divided into a subclass of receptors whose pharmacological characteristics and regional distributions in the central nervous system are distinct.

Clinical studies on compounds with agonist activity for serotoninergic receptors of the 5-HT$_{1A}$ subtype have shown that 5-HT$_{1A}$ agonists are effective in treating anxiety (J. Clin. Psychiatry, 1987, 48, 3S) and depression (Int. J. Neuropsychopharmacology, 1998, 1, 18). Furthermore, studies in animals have shown that 5-HT$_{1A}$ agonists have analgesic properties (Behav. Brain Res., 1995, 73, 1/2, 69) and neuroprotective properties (Arch. Int. Pharmacodyn., 1995, 329, 347).

Given the broad therapeutic potential of compounds with agonist activity for serotoninergic receptors of the 5-HT$_{1A}$ subtype, the discovery of novel compounds with such activity is of great interest in human clinical therapy.

Buspirone, a 5-HT$_{1A}$ agonist used clinically, has comparable affinity for the serotoninergic receptors of the 5-HT$_{1A}$ subtype and for the dopaminergic receptors of the D$_2$ subfamily. Since the dopaminergic receptors of the D$_2$ subfamily are involved in motor control and cognitive and neuroendocrine functions (La Lettre du Pharmacologue, 1997, 11, 3), substances that are active on the dopaminergic receptors of the D$_2$ subfamily, such as buspirone, are thus liable to give rise to neurological and/or motor and/or neuroendocrine disorders (CNS Drug, 1996, 5, 215). Dopaminergic or antidopaminergic activity combined with 5-HT$_{1A}$ agonist activity therefore does not constitute a combination of properties that is desirable for an agent intended for treating neurological disorders that are sensitive to serotoninergic activation mediated by 5-HT$_{1A}$ receptors.

Patent WO 98/22459-A1 discloses pyrid-2-ylmethylamine derivatives of the general formula

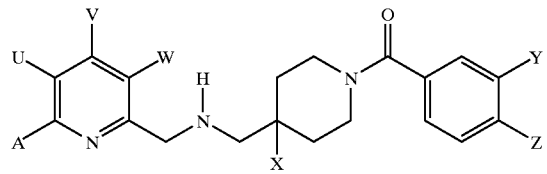

in which:

A, U, V and W are, inter alia, a hydrogen atom,

X represents a hydrogen or fluorine atom,

Y is a chlorine atom or a methyl radical, z is a hydrogen atom, a fluorine atom, a chlorine atom or a methyl radical.

These compounds are claimed as 5-HT$_{1A}$ agonists that are useful in treating disorders that are sensitive to serotoninergic agonists of the 5-HT$_{1A}$ subtype.

The present application relates to novel compounds corresponding to the general formula (1)

formula 1

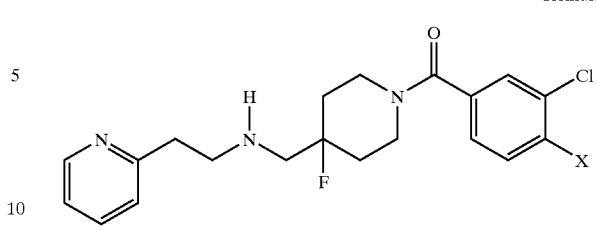

in which:

X is a hydrogen, fluorine or chlorine atom, and to the addition salts and the hydrates of the addition salts of the compounds of general formula (1) with pharmaceutically acceptable mineral acids or organic acids.

The compounds of formula (1) differ from those disclosed in patent WO 98/22459-A1 by the presence of an additional methylene group between the pyridine nucleus and the secondary amine function. The incorporation of the additional methylene group is reflected by a decrease in the dissociation constant of water (Ka) for the compounds of formula (1), by a factor of ten on average, compared with that of the compounds disclosed in patent WO 98/22459-A1. Such an increase in basicity greatly modifies the absorption and distribution parameters and also the modes of in vivo transformation of the compounds of the invention compared with those of the compounds claimed in patent WO 98/22459-A1.

The advantage of the compounds of the invention lies both in their selectivity and in their 5-HT$_{1A}$ agonist activity in vivo, which are much greater than those of buspirone. In this respect, the compounds of the invention, which combine therapeutic efficacy with a low propensity to display adverse side effects of D$_2$ dopaminergic origin such as, for example, neurological and/or motor and/or endocrine disorders, are useful in treating a host of pathologies involving serotoninergic dysfunction, in particular anxiety, depression, neurodegeneration and the perception of pain.

The selectivity is defined in the present application as being the ratio of the affinity constants (Ki) D$_2$/Ki (5-HT$_{1A}$).

The central 5-HT$_{1A}$ agonist activity of the compounds of the invention and of buspirone was evaluated, after oral administration to rats, by their ability to induce retraction of the animals' lower lip (LLR), which is a sensitive and specific marker of central 5-HT$_{1A}$ agonist activity (Pharmacol. Biochem. Behav., 1989, 33, 821).

A subject of the invention is also pharmaceutical compositions containing, as active principle, at least one derivative of general formula (1) or one of its salts or hydrates of its salts in combination with one or more pharmaceutically acceptable excipients, adjuvants or vehicles. By way of example, mention may be made of inclusion complexes, in particular the inclusion complexes formed by the compounds of the invention with β-cyclodextrins.

The pharmaceutical compositions according to the invention are compositions which may be administered orally, nasally, sublingually, rectally or parenterally. It is generally advantageous to formulate such pharmaceutical compositions in unit dose form. In this case, each dose comprises a predetermined amount of the active principle, combined with the appropriate vehicle, excipients and/or adjuvants, calculated to obtain a given therapeutic effect. As examples of unit dose forms which may be administered orally, mention may be made of tablets, gel capsules, granules, powders and oral suspensions or solutions.

The formulations that are suitable for the chosen form of administration are known and described, for example, in Remington, The Science and Practice of Pharmacy, 19$^{th}$ edition, 1995, Mack Publishing Company, and may thus be readily prepared by a person skilled in the art.

It is known that the dosage varies from one individual to another, depending on the nature and severity of the affliction, the chosen route of administration and the weight, age and sex of the patient, and consequently the effective doses will have to be determined as a function of these parameters by the specialist in the field. As a guide, the effective doses may range between 0.001 mg/kg and 100 mg/kg/day.

The compounds of general formula (1) may exist in several tautomeric forms. Such tautomeric forms, although not explicitly reported in the present application to simplify the graphic representation of the formulae, are nevertheless included in the field of application of the invention.

Finally, the invention covers the process for preparing the derivatives of general formula (1).

The compounds of formula (1) were prepared according to the reaction sequence indicated in Scheme A.

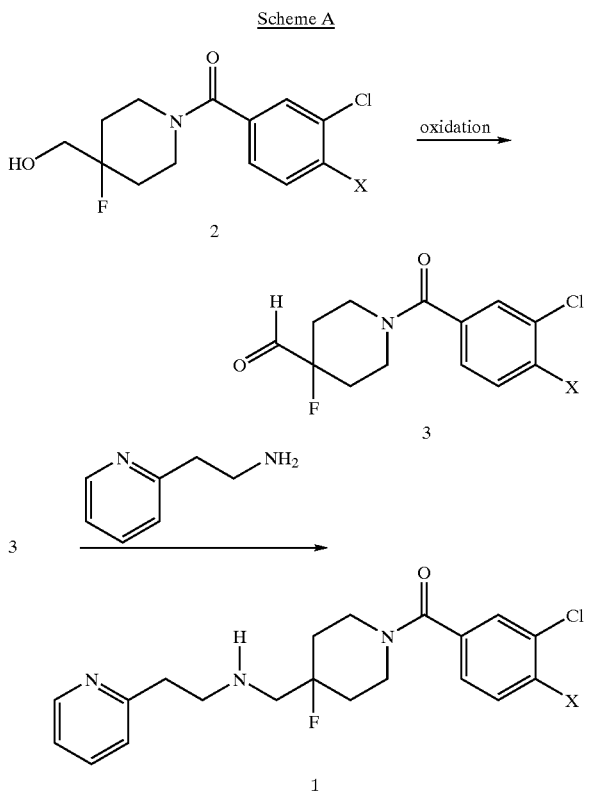

Scheme A

The compounds of formula (2) were prepared according to a method similar to that used for the synthesis of (4-fluoro-4-hydroxymethyl-1-piperidyl) (3-chloro-4-fluorophenyl)methanone and disclosed in patent WO 98/22459-A1. Oxidation of the compound of formula (2), using an activated dimethyl sulfoxide (DMSO) derivative such as, for example, DMSO activated with the sulfur trioxide-pyridine complex or activated with oxalyl chloride, gives the 1-(3-chloro-4-X-benzoyl)-4-20 fluoropiperidine-4-carbaldehyde of formula (3). A reductive amination reaction of the aldehyde of formula (3) using 2-(2-aminoethyl) pyridine, which is commercially available, then gives the compound of formula (1). In the reductive amination reaction under consideration, the aldehyde (3) and the 2-(2-aminoethyl)pyridine are reacted in the appropriate solvent and the mixture is then treated with the reducing agent. The reducing agent under consideration may be a simple or complex boron hydride such as, for example, sodium or potassium borohydride, sodium cyanoborohydride or sodium triacetoxyborohydride.

The examples which follow illustrate the invention without limiting it in any way.

In the examples below:
(i) the reaction progress is monitored by thin layer chromatography (TLC) and the reaction times are consequently mentioned only as a guide.
(ii) different crystalline forms may give different melting points; the melting points reported in the present application are those of the products prepared according to the method described and are uncorrected.
(iii) the structures of the products obtained according to the invention are confirmed by the nuclear magnetic resonance (NMR) and infrared (IR) spectra and the elemental analyses, and the purity of the final products is confirmed by TLC.
(iv) the NMR spectra are recorded in the solvent indicated. The chemical shifts ($\delta$) are expressed in parts per million (ppm) relative to tetramethylsilane. The multiplicity of the signals is indicated by: S, singlet; d, doublet; t, triplet; q, quartet; m, multiplet; b, broad.
(v) the various symbols for the units have their usual meaning: mg (milligram); g (gram); ml (milliliter); ° C. (degrees Celsius); mmol (millimole); nmol (nanomole); cm (centimeter).
(vi) the abbreviations have the following meanings: m.p. (melting point); b.p. (boiling point).
(vii) in the present application, the pressures are given in millibar; the term "room temperature" means a temperature between 20° C. and 25° C.

INTERMEDIATE 1

1-(3-Chloro-4-fluorobenzoyl)-4-fluoropiperidine-4-carbaldehyde (3; X=F)

2.48 g of pyridine-SO$_3$ complex (15.5 mmol) are added in a single portion to a solution of 1.5 g of 1-(3-Chloro-4-fluorobenzoyl)-4-fluoro-4-piperidine-methanol (5.18 mmol), 2.16 ml of triethylamine (15.5 mmol) and 15 ml of anhydrous DMSO. After stirring for 3 hours at room temperature, the yellow solution obtained is poured into an ice-water mixture and extracted twice with ethyl acetate. The organic phases are washed with aqueous 5% citric acid solution and then with salt water, dried over MgSO$_4$ and filtered and the solvent is removed under vacuum. 1.49 g (quantitative yield) of a yellow oil are obtained, this product being used without further purification in the following step.

IR $\upsilon$(C=O) 1735 cm$^{-1}$; $^1$H NMR (CDCl$_3$) $\delta$ 1.50–2.05 (m, 4H); 3.34 (m, 2H); 3.70 (m, 1H); 4.59 (m, 1H); 7.18 (m, 1H); 7.31 (m, 1H); 7.50 (m, 1H); 9.77 (d, 1H).

INTERMEDIATE 2

1-(3,4-Dichlorobenzoyl)-4-fluoropiperidine-4-carbaldehyde (3; X=Cl)

This aldehyde is obtained by the same oxidation technique as that used for the synthesis of Intermediate 1, replacing the 1-(3-chloro-4-fluorobenzoyl)-4-fluoro-4-piperidinemethanol with 1-(3,4-Dichlorobenzoyl)-4-fluoro- 4-piperidinemethanol. A yellow oil is obtained (quantitative yield), which is used without further purification in the following step.

IR υ(C=O) 1743 cm$^{-1}$.

EXAMPLE 1

(3-Chloro-4-fluorophenyl){4-fluoro-4-[(2-pyrid-2-ylethylamino)methyl]-1-piperidyl}methanone (1; X=F)

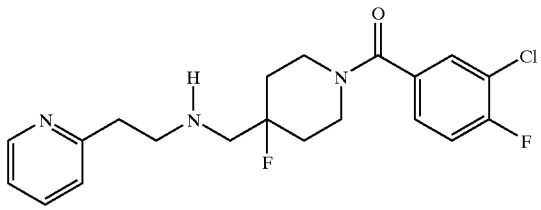

A solution of 1.49 g of 1-(3-chloro-4-fluorobenzoyl)-4-fluoro-4-piperidinecarboxaldehyde (5.18 mmol), 0.70 g of 2-(2-aminoethyl)pyridine (5.70 mmol) and 40 ml of toluene is refluxed with stirring (while removing the water formed using Dean-Stark apparatus) for 2 hours. The toluene is removed by distillation under reduced pressure and the residue obtained is dissolved in 40 ml of anhydrous methanol. 0.55 g of $KBH_4$ (10 mmol) is added portionwise to this solution, with stirring and at room temperature, and the stirring is continued overnight at room temperature. After removing the methanol under vacuum, the residue is extracted twice with ethyl acetate, washed with saline water and then dried over $MgSO_4$ and filtered. The solvent is removed by distillation under vacuum and the product is purified by chromatography on silica, using methylene chloride containing 5% methanol as eluent. 1.43 g (72%) of a pale yellow oil are obtained. Salification with oxalic acid, carried out in an ethanol/ethyl acetate mixture, gives the oxalate in the form of white crystals.

$C_{20}H_{22}ClF_2N_3O \cdot C_2H_2O_4$ (483.91); m.p.: 172–174° C.; $^1$H NMR ($d_6$ DMSO) δ 1.73–1.99 (m, 4H); 3.12 (m, 3H); 3.24–3.32 (m, 5H); 3.47 (m, 1H); 4.30 (m, 1H); 7.28 (q, 1H); 7.32 (d, 1H); 7.46 (m, 1H); 7.52 (t, 1H); 7.68 (d, 1H); 7.76 (t, 1H); 8.50 (d, 1H).

EXAMPLE 2

(3,4-Dichlorophenyl){4-fluoro-4-[(2-pyrid-2-ylethylamino)methyl]-1-piperidyl}methanone (1; x=Cl)

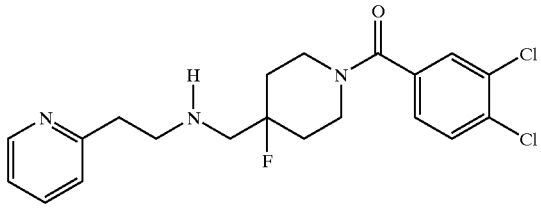

This compound is obtained in the form of the oxalate according to the same procedure as that used to prepare (3-chloro-4-fluorophenyl){4-fluoro-4-[(2-pyrid-2-ylethylamino)methyl]-1-piperidyl}methanone, but replacing the 1-(3-chloro-4-fluorobenzoyl)-4-fluoropiperidine-4-carbaldehyde with 1-(3,4-dichlorobenzoyl)-4-fluoropiperidine-4-carbaldehyde.

$C_{20}H_{22}Cl_2FN_3O \cdot 1.5 C_2H_2O_4$ (545.37); m.p.: 192–194° C.; $^1$H NMR ($d_6$ DMSO) δ 1.70–2.10 (m, 4H); 3.15 (m, 3H); 3.31–3.50 (m, 6H); 4.31 (m, 1H); 7.27–7.41 (m, 3H); 7.69–7.81 (m, 3H); 8.49 (d, 1H).

PHARMACOLOGICAL STUDY OF THE PRODUCTS OF THE INVENTION

The compounds of this invention were compared with 8-[4-[4-(2-pyrimidinyl)-1-piperazilyl]butyl]-8-azaspiro[4.5]decane-7,9-dione (buspirone), which is a 5-$HT_{1A}$ receptor agonist that is used clinically.

1—Measurement of the Affinity of the Compounds of the Invention for the 5-$HT_{1A}$ Receptors

PROTOCOL

The in vitro affinity of the compounds of the invention for 5-$HT_{1A}$ receptors was determined by measuring the displacement of ($^3$H)8-OH-DPAT (TRK 850; 160–240 Ci/mmol).

The study of the binding to the 5-$HT_{1A}$ receptor is carried out as described by Sleight and Peroutka (Naunyn-Schmiedeberg's Arch. Pharmaco., 1991, 343, 106). Rat cerebral cortices are used for these experiments. After thawing the brain in 50 mmol Tris-HCl buffer pH=7.40 at 25° C., the cerebral cortex is removed and homogenized in 20 volumes of buffer maintained at 4°C. The homogenate is centrifuged at 39,000×g for 10 minutes and the centrifugation pellet is suspended in the same volume of buffer and centrifuged again. After resuspending under the same conditions, the homogenate is incubated for 10 minutes at 37° C. and then centrifuged again. The final pellet is suspended in cold 50 mmol Tris-HCl reaction buffer, pH=7.40 at 25° C., containing 10 mmol of pargyline, 4 mmol of $CaCl_2$ and 0.10% ascorbic acid. The final concentration of tissue in the incubation medium is 10 mg/tube.

The reaction tubes contain 0.10 ml of ($^3$H)8-OH-DPAT (0.20 mmol final), 0.10 ml of test product 6–7 concentrations and 0.80 ml of tissue. The nonspecific binding is defined using 10 mmol of 5-HT. The reaction tubes are incubated at 23° C. for 30 minutes and their contents are then rapidly filtered under vacuum through Whatman GF/B filters and the tubes are rinsed with twice 5 ml of 50 mmol Tris-HCl buffer, pH=7.4 at 25° C. The radioactivity collected on the filter is analyzed by liquid scintillation by adding 4 ml of liquid scintillant (Emulsifier Safe, Packard). All the experiments are carried out in triplicate.

2—Measurement of the Affinity of the Compounds of the Invention for the $D_2$ Receptors.

PROTOCOL

The in vitro affinity of the compounds of the invention for the $D_2$ dopaminergic receptors was determined by measuring the displacement of ($^3$H)YM-09151-2 (NET-1004 70–87 Ci/mmol). The study of the binding to the $D_2$ receptor is carried out as described by Niznik (Naunyn-Schmiedeberg's Arch. Pharmacol. Methods, 1985, 329, 333). Rat striatum is used for these experiments. After thawing the brain in 50 mmol Tris-HCl buffer, pH=7.40 at 25° C., the striatum is removed and homogenized in 40 volumes of buffer maintained at 40° C. The homogenate is centrifuged at 20,000×g for 10 minutes and the centrifugation pellet is suspended in the same volume of buffer and centrifuged again. The final pellet is suspended in cold 50 mmol Tris-HCl reaction buffer, pH=7.40 at 25° C. containing 120 mmol of NaCl and 5 mmol of KCl. The final tissue concentration in the incubation medium is 2 mg/tube. The reaction tubes contain 0.20 ml of [³H]YM-09151-2 (0.05 mmol final), 0.20 ml of test product 6–7 concentrations and 1.60 ml of tissue. The nonspecific binding is defined using 1 mmol of (+)-butaclamol. The reaction tubes are incubated at 23° C. for 60 minutes and their contents are then rapidly filtered under vacuum through Whatman GF/B filters and the tubes are rinsed twice with 5 ml of 50 mmol Tris-HCl buffer, pH=7.40 at 25° C. The radioactivity collected on the filter is analyzed by liquid scintillation by adding 4 ml of liquid scintillant (Emulsifier Safe, Packard). All the experiments are carried out in triplicate.

The inhibition constants (Ki) of the products of the invention are estimated from the displacement experiments using the nonlinear regression program RADLIG version 4 from EBDA (Equilibrium Binding Data Analysis) (Biosoft, Cambridge, UK, McPherson, 1985). The dissociation constants of the radioactive ligands used in the calculations are 0.31 mmol for (³H)8-OH-DPAT and 0.036 mmol for (³H)YM-09151-2. The pKi (−logKi) values are given in the form of the mean±SEM of at least 3 experiments.

3—Evaluation of the 5-$HT_{1A}$ Receptor Agonist Activity of the Compounds of the Invention In Vivo.

PROTOCOL

Male Sprague Dawley rats (ICO:OFAD [IOPS], Iffa Credo, France), weighing 160–180 g on arrival and 180–200 g at the start of the tests, are used. The animals are placed in quarantine for 4 to 8 days with free access to standardized laboratory food, before being used in the experiments. The animals are housed individually in plastic cages on cage holders (28 cm×21 cm×18 cm) with a grille floor (RC Iffa Credo), 24 hours before the tests. By means of an automatic dispenser, water filtered through a 0.22 μm filter is freely available. The quarantine area and the experiment laboratory are air conditioned (temperature: 22±1° C.; relative humidity: 55±5%) and illuminated from 7 a.m. to 7 p.m. All the rats are treated according to the ethics for laboratory animals (Guide for the Care and Use of Laboratory Animals, U.S. Department of Agriculture, Public Health Service, National Institutes of Health publication No. 85–23, Revised 1985) and the protocol (No. 15) is carried out in accordance with the recommendations of the local research animals ethics committee.

The methods used are essentially identical to those described above (Drug. Dev. Res., 1992, 26, 21; Eur. J. Pharmacol., 1995, 281, 219).

The behavior of the animal is observed for a period of 10 minutes each, centered at t60 minutes, after oral administration. Four animals are observed individually during the 10-minute period (from t55 to t65); the 4 rats are observed in turn, every 15 seconds, with a 10-second duration of observation per animal. During each of these observation periods, the presence (1) or absence (0) of lower lip retraction (LLR) by the animal is noted. It is considered that there is lower lip retraction if the animal displays uninterrupted signs for at least 3 seconds. This cycle is repeated 10 times over a period of 10 minutes, and thus the frequency of a type of behavior may range from 0 to 10 for each observation period. Each day, two animals from each group receive the same dose of the same product. The products are dissolved in distilled water or are suspended in aqueous Tween 80 solution (2 drops/10 ml of distilled water). The products are administered in a volume of 10 ml/kg and the doses are expressed as base weight. The order of administration of the products and of the doses is randomized.

RESULTS

Table 1 gives, by way of example, the pKis, the selectivity and the active doses ($ED_{50}$) for two derivatives of the invention compared with buspirone, chosen as reference product.

TABLE 1

| Compound | pKi | | Selectivity | LLR p.o. |
|---|---|---|---|---|
| | 5-$HT_{1A}$ | $D_2$ | 5-$HT_{1A}/D_2$ | $ED_{50}$ (mg/kg) |
| Example 1 | 9.81 | 6.18 | 4 266 | 0.31 |
| Example 2 | 9.42 | 6.30 | 1 318 | 0.31 |
| Buspirone | 7.65 | 7.49 | 1.5 | 20 |

The test results show that the compounds of formula (1) have high affinity for the serotoninergic receptors of the 5-$HT_{1A}$ subtype and that they are selective for these receptors, compared with the reference compound.

The in vivo test, performed orally on rats, shows that the compounds of formula (1) exert central 5-$HT_{1A}$ agonist activity which is more powerful than that of the reference compound.

It thus emerges from this study that the compounds of the invention have the advantage of exhibiting not only affinity and selectivity for the serotoninergic receptors of the 5-$HT_{1A}$ subtype which are superior to those of buspirone but also oral 5-$HT_{1A}$ agonist activity which is more powerful than that of buspirone, the 5-$HT_{1A}$ agonist normally used clinically.

In this respect, the compounds of the invention are potentially useful in the treatment of pathologies involving serotoninergic dysfunction such as anxiety, depression, the perception of pain and neurodegeneration.

What is claimed is:

1. A compound selected from those of formula 1

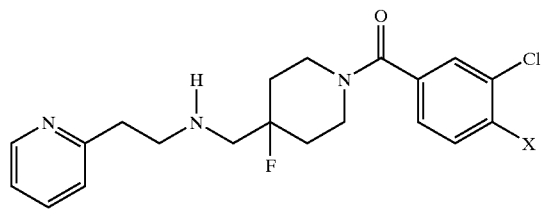

Formula 1 in which X represents a fluorine, chlorine or a hydrogen atom, and its addition salts thereof with a pharmaceutically acceptable mineral acid or organic acid.

2. A compound according to claim 1 which is (3-chloro-4-fluorophenyl) {4-fluoro-4-[(2-pyrid-2-ylethylamino)-methyl]-1-piperidyl}methanone.

3. A Compound according to claim 1 which is (3,4-dichlorophenyl) {4-fluoro-4-[(2-pyrid-2-ylethylamino)-methyl]-1-piperidyl}methanone.

4. A Compound according to claim 1 which is (3-chlorophenyl){4-fluoro-4-[(2-pyrid-2-ylethylamino)-methyl]-1-piperidyl}methanone.

5. A novel synthetic intermediate selected from those of formula 3

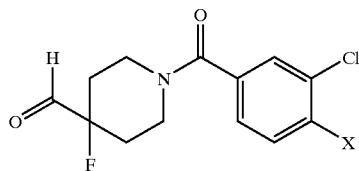

formula 3 in which X is a fluorine, chlorine or hydrogen atom, which are used for the preparation of the compounds of general formula (1).

6. A method of treating a human or living animal suffering from depression, comprising the step of administering to the human or living animal an amount of a compound of claim 1, which is effective for such purpose.

7. A method of treating a human or living animal suffering from pain, comprising the step of administering to the human or living animal an amount of a compound of claim 1, which is effective for such purpose.

8. A method of treating a human or living animal suffering from anxiety, comprising the step of administering to the human or living animal an amount of a compound of claim 1, which is effective for such purpose.

9. A method of treating a human or living animal suffering from neurodegeneration, comprising the step of administering to the human or living animal an amount of a compound of claim 1, which is effective for such purpose.

10. A pharmaceutical composition comprising an effective anti-depressant, analgesic, anxiolytic, or neuroprotective amount of a compound of claim 1 and one or more pharmaceutically acceptable excipients, adjuvants or vehicles.

* * * * *